United States Patent
Eastwood et al.

(10) Patent No.: US 9,284,599 B2
(45) Date of Patent: Mar. 15, 2016

(54) METHOD FOR DETECTING THE PRESENCE OF SPECIFIC MICRO-ORGANISMS AND DEVICE FOR THE SAME

(75) Inventors: Ian Eastwood, Rossendale (GB); Andrew Reid, Beverley (GB); Mark Saw, York (GB)

(73) Assignee: Eluceda Limited, Harrogate (GB)

( * ) Notice: Subject to any disclaimer, the term of this patent is extended or adjusted under 35 U.S.C. 154(b) by 566 days.

(21) Appl. No.: 13/582,236

(22) PCT Filed: Mar. 4, 2011

(86) PCT No.: PCT/GB2011/050432
§ 371 (c)(1),
(2), (4) Date: Nov. 13, 2012

(87) PCT Pub. No.: WO2011/107804
PCT Pub. Date: Sep. 9, 2011

(65) Prior Publication Data
US 2013/0089857 A1    Apr. 11, 2013

(30) Foreign Application Priority Data

Mar. 4, 2010 (GB) .................................. 1003594.7
Dec. 7, 2010 (GB) .................................. 1020652.2

(51) Int. Cl.
*C12Q 1/00* (2006.01)
*C12Q 1/68* (2006.01)
*G01N 33/53* (2006.01)
*C12Q 1/26* (2006.01)
*C12Q 1/32* (2006.01)

(Continued)

(52) U.S. Cl.
CPC .. *C12Q 1/68* (2013.01); *C12Q 1/54* (2013.01); *C12Q 1/6816* (2013.01)

(58) Field of Classification Search
CPC .. C12Q 1/6816; C12Q 2561/125; C12Q 1/28; C12Q 1/30; C12Q 1/32; C12Q 1/68
USPC ........... 435/4, 6.1, 7.1, 188, 287.2, 14, 288.7, 435/25, 26, 27, 28
See application file for complete search history.

(56) References Cited

U.S. PATENT DOCUMENTS

| 4,743,535 A | 5/1988 | Carrico |
| 2003/0124639 A1* | 7/2003 | Wolfbeis et al. ................ 435/25 |
| 2005/0042610 A1 | 2/2005 | Decout et al. |

FOREIGN PATENT DOCUMENTS

| WO | WO-2004/046721 A1 | 6/2004 |
| WO | WO-2008/109617 A1 | 9/2008 |

OTHER PUBLICATIONS

Mogharrab, N. et al., "Structural Stabilization and Functional Improvement of Horseradish Peroxidase upon Modification of Accessible Lysines: Experiments and Simulation", Biophysical Journal, vol. 92, Feb. 2007, pp. 1192-1203.

(Continued)

*Primary Examiner* — Robert T Crow
*Assistant Examiner* — Joseph G Dauner
(74) *Attorney, Agent, or Firm* — Winstead PC

(57) ABSTRACT

A method of testing for the presence of a preselected target nucleic acid, protein or antigen in a biological sample by exposing nucleic acids, proteins or antigens to a probe having a catalytic element and binding element. The catalytic element catalyses at least one reaction that results in a physical change such that identifiable elements provide an indication of the presence of the target.

22 Claims, 6 Drawing Sheets

(51) Int. Cl.
C12Q 1/30 (2006.01)
C12Q 1/28 (2006.01)
C12Q 1/54 (2006.01)

(56) References Cited

OTHER PUBLICATIONS

Personne, P., et al., "Comparative performances of six agglutination kits assessed by using typical and atypical strains of *Staphylococcus aureus*.", Journal of Clinical Microbiology, May 1997, vol. 35, No. 5, pp. 1138-1140.

Davies, S., et al., "Evaluation of a new *Staphylococcus aureus* latex agglutination kit, Prolex Staph Xtra, against other third-generation kits", British Journal of Biomedical Science, Royal Society of Medicine Services, London, GB, vol. 65, No. 3, Jan. 1, 2008, pp. 142-144.
Moller, Robert et al., "Enzymatic Control of Metal Deposition as Key Step for a Low-Background Electrical Detection for DNA Chips", Nano Letters, vol. 5, No. 7, Jul. 1, 2005, pp. 1475-1482.
Holliday, M.G. et al., "Rapid Identification of *Staphylococcus aureus* by Using Fluorescent Staphylocoagulase Assays", Journal of Clinical Microbiology, vol. 37, No. 4, Apr. 4, 1999. pp. 1190-1192.
Franz, Cerstin, "International Search Report" for PCT/GB2011/050432, as mailed Aug. 19, 2011, 7 pages.

* cited by examiner

METHOD FOR DETECTING THE PRESENCE OF SPECIFIC MICRO-ORGANISMS AND DEVICE FOR THE SAME

The present invention relates to a method of testing for the presence of a preselected target nucleic acid, protein or antigen in a biological sample by exposing nucleic acids, proteins or antigens to a probe having a catalytic element and binding element. The invention also relates to a probe suitable for use in the method. The invention has particular benefits in the health service for testing for the presence of infectious agents such as MRSA.

Oligonucleotides from the sample are immobilised and denatured and then exposed to a probe which will anneal or bind to target sequences or sites which are associated with the micro-organism to be detected. The probe also comprises a catalyst (or precursor(s) thereof). The immobilised oligonucleotides are then washed with a mixture of substrate for the catalyst, a second enzyme/substrate pair, matched to the probe system, and identifiable components such as optically active elements. The probe catalyst and substrate are selected such that they will produce a substrate that is a partner in the second catalytic reaction. The reaction of this second system will cause a measurable shift in the physical state of the system, such as a precipitation, polymerisation, colour change or a change in fluorescence, the formation of which will entrap or otherwise affect the identifiable components. It is then possible to assay for the presence of identifiable (for example optically active) components which, if present, indicate the presence of the micro-organism of interest.

Throughout this document the term micro-organism can be taken to cover viruses.

BACKGROUND

Surface-based assays for the detection of oligonucleotides have previously been described. While these assays often include additional steps such as the inclusion of "capture" sequences pre-bound to the surface of the material, or post-assay testing procedures that are effectively visual aids that render a "black box" technology more palatable for market use, the primary issue with the vast majority of systems currently offered is the dependence on the polymerase chain reaction (PCR) to give suitable amplification of the target strand.

Advances in the PCR system since its first inception have reduced the amount of time required to satisfactorily amplify a target oligonucleotide up to detectable levels. However, even real-time PCR systems can take upwards of several hours to produce a definitive positive or negative response, the reaction is sensitive to the presence of contaminants, and repeated cycles of heating and cooling at specific temperature plateaus means that the PCR device is expensive and, with constant use, energy intensive.

The need for a rapid, reliable and economical oligonucleotide testing procedure is steadily growing throughout the world's health services. Although several technologies have seen development in recent years, the primary testing method for infectious agents such as Multi or Methicillin Resistant *Staphylococcus aureus* (MRSA) and strains of *Clostridium difficile* remains the growth of cultures on selective media. For viruses, viral load is determined by methods including PCR, branched DNA (bDNA), and NucliSENS extraction—the latter two examples being more suited to the extraction and quantification of larger viral loads. The necessity of testing for the presence of microorganisms that endanger immuno-compromised individuals (particularly in hospitals) such as MRSA has been recognised in proposed legislation from the UK and USA governments. Current testing methods are slow or require specialist technical skill with complicated laboratory facilities which are unsuitable for some hospital situations.

Aside from medical use, the testing method could be readily used to identify the presence of micro-organisms in the environment, such as in soil and water for agricultural and hygiene testing, and in forensic applications for the transfer of biologically-derived materials.

SUMMARY OF THE INVENTION

One aspect of the invention provides a method of testing for the presence of a preselected target nucleic acid as claimed in Claim 1.

Another aspect of the invention provides a method of testing for the presence of a preselected target protein or antigen as claimed in Claim 19.

Another aspect of the invention provides an assay as claimed in Claim 31.

Yet another aspect of the invention provides an assay as claimed in Claim 32.

Another aspect of the invention provides a probe as claimed in Claim 34.

Another aspect of the invention provides a kit as claimed in Claim 35.

One aspect of the invention provides a method of testing for the presence of a target nucleic acid sequence comprising the steps of:

exposing nucleic acid sequences from a sample to a probe under hybridisation conditions the probe comprising a first catalytic element or precursor thereof and a binding element capable of binding at least partially to the target nucleic acid sequence, exposing the nucleic acid sequences to:

identifiable elements at least a first substrate, said substrate being capable of reaction with the first catalytic element under conditions which result in a physical change, detecting the physical change and wherein the first catalytic element is a catalytic element that is capable of a turnover rate of greater than 3000 molecules per second, Preferably, the physical change is a pH change and/or a visible change.

One aspect of the invention provides a method of testing for the presence of a target nucleic acid sequence comprising the steps of:

exposing nucleic acid sequences from a sample to a probe under hybridisation conditions the probe comprising a first catalytic element or precursor thereof and a binding element capable of binding at least partially to the target nucleic acid sequence, exposing the nucleic acid sequences to:

identifiable elements at least a first substrate, said substrate being capable of reaction with the first catalytic element under conditions which result in a physical change and the physical change causes the identifiable elements to be entrapped or otherwise retained against removal by washing, substantially in the vicinity of the probe and wherein the first catalytic element is a catalytic element that is capable of a turnover rate of greater than 3000 molecules per second.

This provides the advantage that when the probe is bound to the target, the identifiable elements are entrapped or otherwise retained substantially in the vicinity of the bound probe.

This also provides the advantage that the first catalytic element quickly converts the first substrate to a product useful in a second reaction.

In a preferred embodiment, the first catalytic element is a catalytic element capable of a turnover rate of around 40,000,000 molecules per second.

The first catalytic element may be a catalyst or at least one catalytic precursor. The first catalytic element may be any suitable catalytic or enzymatic species.

In a preferred embodiment, the first catalytic element comprises catalase and the first substrate comprises a peroxide.

Hybridisation conditions may comprise heating the target sequences at a plateau of 80-100° C. and more specifically 90-98° C. Then cooling to a plateau in the region 50-65° C. (depending on the nature of the probe(s) used), and washing a surface on which the sequences are immobilised, with probe and allowing to cool and anneal.

In a preferred embodiment, the conditions comprise the step of exposing the nucleic acid sequences to a second substrate and a second catalytic element. This provides the advantage that coupled reactions may increase reaction times. In one embodiment the method may provide a cascade of reactions, which may be more than two reactions.

Advantageously, the product of the reaction of the first substrate and first catalytic element comprises a catalyst or substrate for the reaction of the second substrate and second catalytic element.

The physical change may comprise a pH change, degeneration, gelation, coagulation, precipitation, change in optical density, change in colour, change in fluorescence, polymerisation and/or cross-linking.

Preferably the conditions comprise the step of exposing the nucleic acid sequences to a conversion substrate. This provides the advantage that the conversion substrate is capable of undergoing conversion to a physical change.

In one embodiment the physical change is a pH change which in turn causes a further physical change in the conversion substrate, such as polymerisation/precipitation.

Preferably, the physical change comprises formation of a three dimensional polymer network.

In a preferred embodiment, the physical change is a physical change of the conversion substrate, which is effected by the product of the reaction of the first substrate and first catalytic element and/or the product of the reaction of the second substrate and second catalytic element. The conversion substrate may be a monomer that undergoes conversion to a polymer in response to the presence of a particular product in the reaction mixture.

The method may comprise the preliminary steps of rendering the nucleic acid sequences available, and immobilising the nucleic acid sequences.

The method may comprise at least one washing step. A final washing step may comprise a wash comprising a reagent that promotes cross-linking of polymer chains.

Advantageously, the identifiable elements are identifiable by photonic, optical or electrical measurement. This provides the advantage that the physical change affects whether identifiable elements will be present or present in a particular form or quantity, which in turn provides an indication of the presence or absence of the target.

In one embodiment, the identifiable elements comprise a pH indicator or indicators.

In a preferred embodiment, the identifiable elements comprise optically active elements.

Advantageously, the optically active particles are sufficiently small to not block fluid flow across or past the slide/filter surface.

The physical change may cause fluid flow across or past the slide/filter surface to be blocked.

The optically active particles may comprise substantially sub-micrometer sized phosphors.

Preferably, the method comprises the step of testing for the presence of identifiable components by exciting the optically active particles with light and measuring the response. Thus, light of a suitable wavelength can be used to excite the particles and the emitted response can be measured.

In one embodiment, the method may comprise the step of detecting a photonic response using a photomultiplier tube. In this embodiment the response maybe a photonic response requiring no excitation and the cumulative total of photons released may be measured.

Preferably, the method comprises the step of comparing the response to a predetermined threshold value. The predetermined threshold is consistent with the signal required to distinguish the presence of optically active particles from background "noise".

The binding element may be an oligonucleotide sequence complementary to the target nucleic acid sequence. The oligonucleotide may comprise DNA, RNA or a stable analogue thereof.

Another aspect of the invention comprises a method of testing for the presence of a target protein or antigen comprising the steps of:
    exposing proteins or antigens from a sample to a probe the probe comprising a first catalytic element or precursor thereof and a binding element capable of binding at least partially to the target protein or antigen,
    exposing the proteins or antigens to:
    identifiable elements
    at least a first substrate, said substrate being capable of reaction with the first catalytic element
    under conditions which result in a physical change and the physical change causes the identifiable elements to be entrapped or otherwise retained against removal by washing, substantially in the vicinity of the probe
    and wherein the first catalytic element is a catalytic element that is capable of a turnover rate of greater than 3000 molecules per second.

In a preferred embodiment, the first catalytic element is a catalytic element capable of a turnover rate of around 40,000,000 molecules per second.

The probe may comprise an antibody or aptamer.

In a preferred embodiment, the first catalytic element comprises catalase and the first substrate comprises a peroxide.

Preferably, the conditions comprise the step of exposing the proteins or antigens to a second substrate and a second catalytic element.

Advantageously, the product of the reaction of the first substrate and first catalytic element comprises a catalyst or substrate for the reaction of the second substrate and second catalytic element. This provides the advantage that coupled reactions may increase reaction times. In one embodiment the method may provide a cascade of reactions, which may be more than two reactions.

The physical change may comprise a pH change, degeneration, gelation, coagulation, precipitation, change in optical density, change in colour, change in fluorescence, polymerisation and/or cross-linking.

Preferably, the conditions comprise the step of exposing the proteins or antigens to a conversion substrate.

In a preferred embodiment, the physical change comprises formation of a three dimensional polymer network.

Advantageously, a physical change of the conversion substrate is effected by the product of the reaction of the first substrate and first catalytic element and/or the product of the reaction of the second substrate and second catalytic element.

The method may comprise the preliminary steps of rendering the proteins or antigens available, and immobilising the proteins or antigens.

Preferably, the method comprises at least one washing step. The wash may comprise a reagent that promotes cross-linking of polymer chains.

Advantageously, the identifiable elements are identifiable by photonic, optical or electrical measurement.

Preferably, the identifiable elements comprise optically active elements.

Advantageously, the method of the invention detects the presence or absence of a micro-organism of interest in the sample. In one embodiment, the term "absence" may be interpreted to mean that the target is not present above a specific threshold value.

The micro-organism may be methicillin resistant *Staphylococcus aureus* (MRSA).

The catalytic element may comprise at least one catalytic precursor.

In one embodiment the catalytic element comprises at least one catalytic precursor and the method comprises the step of exposing the nucleic acid sequences or proteins or antigens to an activating element that adds a catalyst to the at least one catalytic precursor binding site or reacts with the at least one catalytic precursor to form a catalyst.

Another aspect of the invention provides an assay for detecting the presence of a target nucleic acid sequence by testing for the presence of optically active elements entrapped or otherwise retained against removal by washing, substantially in the vicinity of a probe.

Yet another aspect of the invention provides an assay for detecting the presence of a target protein or antigen by testing for the presence of optically active elements entrapped or otherwise retained against removal by washing, substantially in the vicinity of a probe.

Another aspect of the invention provides a probe suitable for use in the method of any of claims 1 to 29, wherein the first catalytic element is selected to initiate a reaction or multiple reactions resulting in a physical change.

The probe may comprise a spacer or linker between the catalytic element and binding element of more than 13 carbon-carbon bonds or equivalent in length. For example, this could be a compound such as biotin linked to the probe by a spacer of 6 to 12 carbon-carbon bonds (or equivalent) and more preferably 8 carbon-carbon bonds (or equivalent) that would bind avidin linked to the first catalyst.

Another aspect of the invention provides a kit comprising a probe and instructions for use in the method of the invention.

The kit may comprise a cassette, slide or cartridge.

The kit may comprise apparatus for of testing for the presence of optically active particles.

Another aspect of the invention provides apparatus for detecting the presence of a micro-organism of interest in a sample, comprising a sample receiving portion, means for optically analysing the sample, means for heating and cooling the sample and means for indicating a positive or negative result An alternative embodiment of the invention provides a method of testing for the presence of a target nucleic acid sequence, protein or antigen comprising the steps of:

exposing nucleic acid sequences, proteins or antigens from a sample to a probe under hybridisation conditions the probe comprising a first catalytic element or precursor thereof and a binding element capable of binding at least partially to the target, exposing the nucleic acid sequences, proteins or antigens to:

identifiable elements at least a first substrate, said substrate being capable of reaction with the first catalytic element under conditions which result in a physical change and the physical change causes a colour change or change in fluorescence substantially in the vicinity of the probe.

Preferably the method is under conditions which are amenable to a physical change from the results of a reaction between the substrate and catalytic element which in turn causes a colour change or change in fluorescence substantially in the vicinity of the probe.

BRIEF DESCRIPTION OF THE DRAWINGS

In order to provide a better understanding of the present invention, embodiments will now be described by way of example only and with reference to the following drawings in which.

DETAILED DESCRIPTION OF THE PREFERRED EMBODIMENTS

Figure 1:
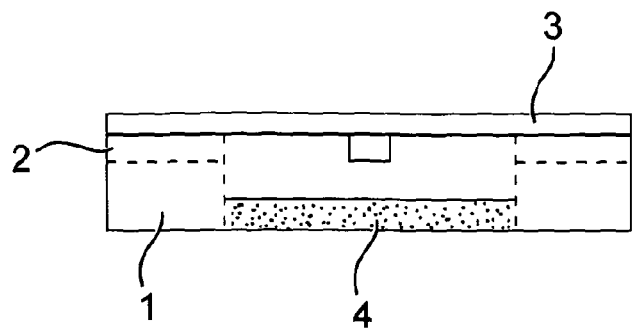
FIG. 1 shows a side view of the disposable slide for oligonucleotide detection.

The invention relates to a method and device for the identification of at least one predetermined analyte such as DNA, RNA, protein or antigen that acts as a marker for a pathogen that may exist within a sample, and test methods to bring about the positive or negative confirmation of such presence. The invention is further related to the construction and use of a disposable cassette, cartridge or slide to contain the sample, allow access and concurrent flow of fluid across or past the sample and allow measurement of the optical, electrical, or similarly measurable response following the assay treatment.

An alternative embodiment of the invention relates to a method for identifying at least one protein that is known to be associated with the presence of a specific micro-organism.

A general overview of the invention is that the target organisms are collected from a surface (inanimate object or an individual) with a swab, or sample (such as blood, tissue or urine) with a pipette. The organisms are then washed into a well containing buffers and reagents to lyse the microorganisms (or at least to destroy the integrity of their membranes) and free and protect the nucleic acids or proteins. The well is part of a disposable unit that has filtration and a method to transport the nucleic acids with or without the remaining microorganism components to a solid matrix that will capture the nucleic acids or proteins.

The target oligonucleotide strand is bound to a portion of the slide or filter membrane, and all remaining unbound solids are denatured and washed off or filtered using a wash mixture that also prevents the slide from binding any further oligonucleotides.

Following washing, the surface is heated to denature the double-stranded oligonucleotide and cooled in the presence of at least one probe molecule. The probe contains both a complementary sequence to the target strand, and either a catalytic or enzymatic moiety, or a precursor to which a catalytic or enzymatic moiety can be linked in a subsequent reaction step.

Following the generation of a target-probe conjugate featuring a catalytic species (obtained by either of the routes described), the slide is washed to remove all unbound probe. The assay step is to flood the slide with a mixture of substrate specific to the action of the catalyst/enzyme; this reaction is chosen such that the presence of the catalyst produces a rapid increase in the concentration of a known product. The mixture contains, further to the initial substrate, a second catalyst species that undergoes reaction specifically with the product of the probe catalysis. By this method, an artificial enhancement of the second catalytic reaction is produced. The final portion of the assay system is the inclusion of a marker compound and an optically active particle, such that if the probe catalyst is present, the cascade of reactions produces a measurable shift in the reaction conditions, such as the precipitation of the marker compound/conversion substrate or its degeneration to form a polymeric species. By either means, the optically-active particle is trapped within the reaction well (trapped by blockage of the filter by the polymeric species).

The slide is washed a final time, and the slide surface analysed using an optical method specific to the optically active particles to determine if they have been trapped. If the reaction produces another measurable shift such as a change in optical density, colour or fluorescence, the measurement is taken directly using a suitable source and detector. Hence, by any method of detection, if the target strand is present, it will yield a qualitative yes/no response for the presence of the desired oligonucleotide or other marker of interest.

The invention provides a method for detecting the presence of a micro-organism of interest in a sample, comprising the steps;
rendering the protein or RNA/DNA in the sample available; and
Immobilising any nucleic acids or proteins present in the sample; exposing the immobilised nucleic acids or antigen to a probe under hybridisation conditions, said probe comprising a binding element capable of specifically binding to a specific nucleic acid or protein and an element capable of initiating the catalytic conversion of a substrate into a predetermined product; and
exposing the immobilised nucleic acids to a mixture of identifiable elements, substrate for the probe catalyst, a second catalytic element capable of reaction from the turnover of probe catalyst, and compound capable of undergoing a physical change upon action of the second catalytic element;
removing any free or unbound mixture;
assaying for the presence of the identifiable element;
wherein the elements capable of initiating physical change and substrate are selected to together produce a detectable change in the optically active elements or a polymer network which will entrap optically active elements.

The probe is adapted to bind to elements of a micro-organism, such as a particular gene, that is specific to the microorganism of interest. Therefore the probe will only bind if the micro-organism of interest is present. The probe is also adapted to have an element capable of initiating polymerisation in the form of a catalyst at one end (or precursor thereof) so when a substrate for the catalyst is provided, the catalyst and substrate will together act to produce a product at a significant rate of generation. The product of this reaction will act as a partner in a second catalyst/substrate reaction that will produce a large, measurable change of state, such as the formation of a three dimensional polymer structure which entraps optically active-elements close to the probe during its formation such that they cannot be washed off. The presence of optically active elements can then be measured or identified, and the presence of said elements is indicative of the presence of the micro-organism of interest.

Preferably the identifiable element is an optically active element.

Notably, the method will identify the presence of a micro-organism of interest without requiring either a pre-binding capture step that requires only nucleic acids or proteins of interest to be immobilised, or a polymerase chain reaction (PCR) step.

Throughout this Application catalytic element can be taken to cover enzymatic element.

The stringency of hybridisation can be controlled by temperature, ionic strength, pH, and the presence of denaturing agents such as formamide during hybridization and washing. Conditions routinely used are set out in readily available procedure texts (e.g. Current Protocol in Molecular Biology, Vol. 1, Chap. 2.10, John Wiley & Sons, Publishers (1994); Sambrook et al., Molecular Cloning, Cold Spring Harbor (1989)).

Optionally the protein or RNA/DNA in the sample is made available by lysing cells present in the sample.

More specifically the method may comprise the steps;
Lysing cells present in the sample; and
Immobilising any nucleic acids present in the sample;
Denaturing the nucleic acid;
Exposing the immobilised nucleic acids to a probe under hybridisation conditions, said probe comprising a complementary oligonucleotide capable of specifically binding to a specific nucleic acid and a catalytic element; and
Exposing the immobilised nucleic acids to a mixture of optically active elements, substrate for the probe catalytic element, a second catalyst and such substrates and other compounds as required for the catalytic element
wherein the catalytic elements and substrates are selected to together act to produce a polymer network which will entrap optically active elements.

An alternative method comprises the steps;
Lysing cells present in the sample; and
Immobilising any nucleic acids present in the sample;
Exposing the immobilised proteins to a probe under hybridisation conditions, said probe comprising a complementary oligonucleotide capable of specifically binding to a specific nucleic acid, and a catalytic element; and
Exposing the immobilised proteins to a mixture of optically active elements, substrate for the probe catalytic element, a second catalyst and such substrates and other compounds as required for the catalytic element.
Wherein the catalytic elements and substrates are selected to together produce a change in optical density, colour or fluorescence.
An alternative method comprises the steps;
Lysing cells present in the sample; and
Immobilising any nucleotide, protein or antigen marker present in the sample;
Exposing the immobilised nucleotide, protein or antigen marker to a probe, said probe comprising an binding agent capable of specifically binding to a specific nucleotide, protein or antigen, and a catalytic element; and
Exposing the immobilised nucleotide, protein or antigen marker to a mixture of optically active elements, substrate for the probe catalytic element, a second catalyst and such substrates and other compounds as required for the catalytic element.
Wherein the catalytic elements and substrates are selected to together produce a polymer network which will entrap optically active elements.
An alternative method comprises the steps;
Lysing cells present in the sample; and
Immobilising any nucleotide, protein or antigen marker present in the sample;
Exposing the immobilised nucleotide, protein or antigen marker to a probe, said probe comprising a binding agent capable of specifically binding to a specific nucleotide, protein or antigen, and a catalytic element; and
Exposing the immobilised nucleotide, protein or antigen marker to a mixture of optically active elements, substrate for the probe catalytic element, a second catalyst and such substrates and other compounds as required for the catalytic element.
Wherein the catalytic elements and substrates are selected to produce a change in optical density, colour or fluorescence.

Preferably the optically active particle is sufficiently small to not block fluid flow across the slide surface. Optionally the optically active particle is a sub-micrometer sized phosphor.

Preferably the presence of any optically-active particles is assayed by exciting the particles with light of a suitable wavelength and measuring the emitted response.

Most preferably the measured emitted response is compared to a predetermined threshold consistent with the signal required to distinguish the presence of optically active particles from background "noise".

Preferably the probe comprises a binding element, a spacer and a catalyst.

The spacer or linker molecule is a molecule of sufficient length that it will prevent the catalytic element of the probe interfering with the binding of the binding element to the nucleic acid or protein of interest.

Alternatively the probe may comprise a binding element, a spacer and a catalytic precursor.

In the case where the probe comprises a catalytic precursor, the method may comprise the additional step of exposing the immobilised nucleic acids or proteins to an activating element which either adds the catalyst to the precursor binding site or acts on the precursor to form the catalyst.

Preferably the binding element is an oligonucleotide sequence selected to be complementary to a known nucleic acid that would be present in the target micro-organism.

The oligonucleotide sequence is generally composed of DNA, RNA or a stable analogue thereof.

The invention also provides a device for detecting the presence of a micro-organism of interest in a sample, comprising;
A sample receiving well in fluid communication with a solid matrix to capture nucleic acids, proteins and/or antigens;
Means for providing various reagents and solutions to the matrix;
A means for optically analysing said matrix.

Providing a device of this type that will automate the method of the first aspect provides a sample handling system that requires minimal user intervention in order to identify the presence of specific micro-organisms in a sample.

More specifically the device may comprise;
A sample receiving well in fluid communication with a solid matrix to capture nucleic acids;
A means for heating and cooling said matrix;
Means for providing various reagents and solutions to the matrix;
A means for optically analysing said matrix.

Preferably the device further comprises a display for indicating results of the analysis to a user, such as a red or green diode (indicating something such as fail and pass respectively).

Most preferably the display is an LCD screen. Preferably the device comprises a CPU.

In the preferred embodiment, the presence of a target oligonucleotide is determined by first binding all oligonucleotides present in a sample to a slide. This is washed to remove extraneous compounds, denatured and washed with probe molecules in such a manner that if the target strand is present, the complementary probe(s) will be bound to the surface via the target strand and will have a catalyst or enzyme present at their terminal end. The presence of this catalytic species is assayed by the addition of a substrate, a second catalyst, and optically-active particle mixture; the substrate chosen such that a polymeric network is formed by the cascade action of the catalytic species in turn and the optically-active particles are held in the vicinity of the slide against the action of further washes by this gel. The slide is then tested via an optical device for the presence of the optically-active particles above a set threshold to determine whether gelation has taken place and hence the presence of the target strand.

The present invention is directed towards the detection of target oligonucleotide sequences in a chosen sample. Target sequences include DNA and RNA, including all forms of mRNA, hrRNA, rRNA and tRNA. The invention can also cover antigen recognition with antibodies, markers recognised by aptamers, or in fact any form of specific binding pair such as a binding protein and its target The present invention may be used to detect specific oligonucleotides present in a wide variety of biological samples, including but not limited to bodily fluids such as whole blood, serum, plasma, saliva, urine, lymph, spinal fluid, tears, mucus, semen and the like, agricultural products, food items, waste products, environmental samples (such as soil and water samples), moist swabs taken from surfaces such as skin or objects, or any other sample containing or suspected to contain oligonucleotide sequences of interest.

The present invention may also be used to detect oligonucleotides present in non-biological samples or in purified or amplified states, such as those that have been pre-amplified via the polymerase chain reaction (PCR), but such pre-treatment of the sample is optional and not mandatory in this invention.

The present invention may be used to detect the presence of individual strains and species of microorganisms, such as viruses or bacteria, by detecting the presence of their unique nucleic acid sequences in a sample of any kind as mentioned above. Other uses of the invention will be immediately apparent to those skilled in the art.

Sampling, Oligonucleotide Separation and Binding

A swab is applied to the area to be tested for microorganisms. The swab is then submerged in a buffered solution containing constituents appropriate for the extraction and stabilisation of the nucleic acids present in the microorganisms. The solution will contain a chemical that assists in the lysis of the microorganisms that could be a detergent or an enzyme, examples of which are sodium dodecyl-sulphate (SDS) and lysozyme. The buffered solution will be formulated to stabilise and to prevent enzymes from destroying the nucleic acids once extracted. The solution may also contain enzymes that cleave the chromosomal DNA in order to render it more susceptible to denaturation.

The solution may be optimised to allow an electric current to be applied in order to separate proteinaceous and nucleic acid material by electrophoresis. It may be optimised to assist in the transfer of the nucleic material onto a nitrocellulose membrane by vacuum pressure or fluid movement through a nitrocellulose membrane. There may also be constituents of the solution that break the proteins and glycoproteins into smaller, more manageable sizes. The solution in the swab receptacle may be formed by the addition of pure, sterile water to dried solution constituents (lyophilised). The receptacle may have the ability to be heated to a temperature that assists in the lysis of the microorganisms or may have an electrical contact to allow the application of a current across the receptacle or be itself a sonication device with the capability of applying ultrasonic energy to the solution or the walls of the receptacle may be UV-transparent to allow the application of ultraviolet light.

The transfer of nucleic acids to a solid matrix for capture is accomplished by one of several methods. An example of the matrix that captures the nucleic acids is nitrocellulose or a derivatised form of nylon. In one method the contents of the receptacle are channelled onto the solid matrix by vacuum pressure that draws the solution through the matrix. In another, the nucleic acids are drawn onto the matrix by electrophoresis with a current applied to a continuous buffer from behind the matrix and at the swab receptacle. This latter method has the benefit of separating the proteinaceous and the nucleic acid material by ionic charge. The nucleic acids adhere to the solid matrix because of ionic charge.

Attachment is encouraged by the use of heat, negative pressure through the backing plate that draws the oligonucleotide into close contact with the binding layer and alkaline conditions and optionally UV light.

Blocking Non-Specific Binding and Removal of Protein

After the oligonucleotides are bound to the surface, the slide can be heated or washed with a buffer containing species such as ethanol, methanol, acetic acid, trichloroacetic acid, urea, dithiothreol, or tris(2-carboxylethyl)phosphine to denature and remove any protein, organic, inorganic salt or other molecular species that may interfere with the assay. Following this, the slide surface is washed with a blocking solution to prevent any future non-specific binding of oligonucleotides (more specifically, probe strands) to the nitrocellulose. This blocking solution can be a buffer containing bovine serum albumen (BSA), salmon sperm DNA or any other DNA that is unlikely to carry the sequences of interest and/or Denhardt's solution.

Probes

Probes are composed of three specific sections. The first is an oligonucleotide sequence complementary to a portion of the target strand, composed of either DNA or a suitably stable analogue that will afford increased binding affinity (such as non-phosphodiester backbones). The probe might also be a polypeptide sequence (such as a protein) capable of binding to a specific site or target on the cell or coat.

The second is a linker molecule of sufficient length to allow binding to occur between target strand and probe without the third portion causing interference with the binding efficiency. This linker may be, for example, alkyl, aryl, ssDNA, a ring-opened succinate or any other species that may be immediately apparent to those skilled in the art.

The third portion is one of the following; a catalytic species, such as: oxidase, catalase, amylase, or phosphatase. Junction between this third portion and the linker can be effected by a method such as, but not limited to the streptavidin-biotin interaction, or a Diels-Alder cyclisation between the two species such that the connection can be made prior to, or during the course of the testing sequence. Other attachment methods that occur in aqueous solution and are capable of producing a bond that can withstand the assay conditions may also include: esterification, amide formation, nucleophilic substitution, electrophilic substitution, substitution-elimination processes or any other bond formation processes that may be apparent to those skilled in the art.

Probe Application and Binding

The target sequences are heated to effect denaturation of the double-stranded oligonucleotides at a plateau of 80-100° C. and more specifically 90-98° C. This is cooled to a plateau in the region 50-65° C. (depending on the nature of the probe(s) used), and the surface washed with probe. This is allowed to cool and anneal, such that if the target sequence is present, the probe and the pendant catalytic group are now attached to the surface via the target-probe binding.

Surface Assay Mixture

The surface assay mixture is a buffer base that includes four major components; a substrate for the probe catalyst, a second catalyst/substrate system, precursors for gelation or precipitation, and an optically active particle. One example is outlined below:

EXAMPLE 1

Catalase Probe—amount as required (depends on amount in target but typically $10^6$ molecules)

Peroxide—0.3%

Casein (Oxoid) 0.1% used as buffer/stabiliser.

Glucose 100 mM used in a 2 ml glass vessel with lid on to avoid air.

Visible precipitation is noticeable within five minutes.

Preferably the surface assay mixture is a solution in which the reagents are free to diffuse.

The substrate identity is dependent on the nature of the probe catalyst. Each enzyme family has specific substrates that can be individually tailored to the system, but more importantly, each has a known product. For example, many oxidases produce hydrogen peroxide, catalase produces oxygen, amylases produce carbon dioxide and sugars (dependent on the substrate), and phosphatases can produce phosphoric acid, among other products. The nature of this product determines the choice of the second catalyst system.

Preferred probe catalysts are those with high turnover rates—preferably enzymes having a turnover rate of over 3000 molecules of substrate per second, such as catalase, carbonic anhydrase or acetylcholine esterase.

The second catalyst/substrate system can be chosen from a wider range of catalysts; the product of the probe catalyst should be an essential part of the catalyst system, but is not necessarily the primary substrate.

For example, the use of catalase as the probe enzyme would couple well with a glucose oxidase system that, in the presence of the oxygen produced due to the breakdown of hydrogen peroxide, would produce gluconic acid that will cause the pH of the reaction system to drop. Combined with a protein that gels on acidification, such as casein, the reaction system is complete.

Figure 14:
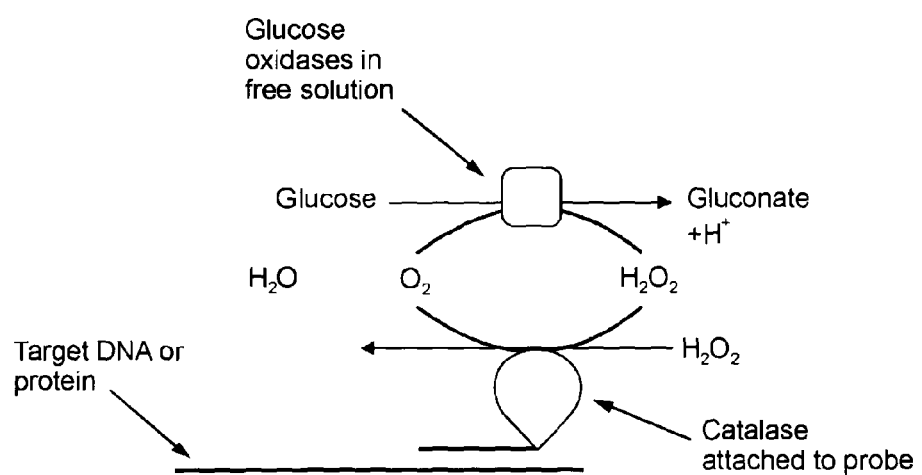
FIG. 14 shows a schematic representation of one embodiment of the invention comprising catalase as the probe enzyme.

FIG. 14 shows the reaction of catalase and the use of an oxidase enzyme to detect the oxygen product from the reaction of peroxide with catalase. If the catalase on the probe is present it generates oxygen that is then converted by free glucose oxidase to gluconic acid and this causes casein to precipitate.

As a final step, fluid can be sucked through a filter. If the catalase is not present, there is no precipitate so the filter does not block and there is no fluorescent liquid left in the filter well.

If there is no catalase, there is no pH shift, casein does not precipitate so the filter does not block and the liquid and fluorescent (or other detection) agent goes right through the filter to waste so we don't detect it.

In this embodiment, the probe is associated with a first catalytic element catalase, which reacts with a first substrate hydrogen peroxide to form a first product oxygen. The second catalyst is glucose oxidase, which catalyses the conversion of a second substrate—glucose and the oxygen produce of the first reaction, to form gluconic acid. The pH change caused by production of gluconic acid causes a conversion substrate—casein—to form a gel or precipitate, which entraps or otherwise retains optically active elements in the gel.

A major advantage of using catalase as the first catalytic element is that this produces a very fast reaction time. The test will provide a result in under 10 minutes and more preferably in under 2 minutes. Glucose oxidase could be included at approximately 0.1-1 mg/ml and more preferably less than or equal to about 0.3 mg/ml.

Catalase is one of the fastest enzymes. Some 40 million molecules of hydrogen peroxide can be converted to water and oxygen per second—generating some 20 million molecules of oxygen.

The extremely high turnover rate of the probe enzyme ensures that the first reaction takes place quickly such that an abundance of the first reaction product is readily available to take part in the second reaction.

Catalase, as the probe enzyme, has a turnover number of around 10 times that of glucose oxidase—the second enzyme. Thus, enzymes having a turnover rate of over 3000 molecules of substrate per second are useful in the invention as the probe catalyst.

By contrast other enzymes commonly used in assays such as glucose oxidase are capable of converting substrate to product at some 283 molecules per second (Takamura 1962) and Horse radish peroxidise works at 334 per second (Biophys J. 2007 Feb. 15; 92(4): 1192-1203.), which is in the order of about $1.67 \times 10^5$ times slower.

It is difficult to measure the outcome of the catalase reaction ie the production of oxygen and water. Measuring the amount of oxygen released by the catalase attached to a bound probe and all adjusting the amounts of the other reagents accordingly (for example by adding an excess of hydrogen peroxide and glucose) can produce an assay roughly 60,000 times faster or more sensitive.

The problem is that measuring oxygen is not simple. However, measuring a coupled reaction with, for example, glucose oxidase is achieveable.

Glucose oxidase uses oxygen and glucose to produce gluconic acid and a molecule of hydrogen peroxide. The gluconic acid changes the pH of the system, which can be detected by a pH probe, a pH indicator or it can create a physical change such as a polymerisation or precipitation of a substrate in solution.

Glucose oxidase catalyses the reaction of the product of the probe enzyme reaction (oxygen). However, glucose oxidase is some 60,000 times slower than catalase and therefore it is necessary to include an excess of materials for the second reaction. This is done by adding a vast excess to the bulk liquid surrounding the reaction. Doing so ensures that the rate of the reaction is dependent upon the amount of catalase present and not the glucose oxidase. There is also an excess of hydrogen peroxide and the other substrate, glucose.

The glucose oxidase reaction produces gluconic acid and peroxide. This poses a slight problem in that the reaction is reversible. High levels of peroxide actually reduce the rate of reaction of the enzyme and at a concentration of 0.3% peroxide, the reaction could reverse if appreciable levels of gluconic acid are present. This can affect the sensitivity of the assay. However, surprisingly, it has been found to ensure the reaction as a cascade—when the oxygen tension rises, the level of peroxide drops pushing the reaction in the forward direction. Moreover, there is a slight self-perpetuating effect as a consequence of the peroxide generated by the glucose oxidase, which means that the same results can be achieved using a 50% lower peroxide concentration than would be expected.

The skilled reader will appreciate that this reaction is preferably performed in a closed vessel so that there is no interference from oxygen entering the system from the atmosphere.

In the embodiment described above, the oxygen produced by the first reaction participates in a second reaction to effect a pH shift, which causes polymerisation/precipitation. The enzymes and reagents in the second reaction are free in solution and are preferably present in excess so that the rate limiting step is not the second reaction.

An additional feature of the reaction is that the second reaction is reversible and a substrate in the first reaction actually inhibits the forward reaction of the second reaction. This actually provides an advantageous effect because high peroxide levels inhibit the glucose oxidase reaction, so that only if catalase is present (ie probe has bound) can the level of peroxide drop and the glucose oxidase start working.

The system uses a pH shift to start the precipitation reaction. The probe enzyme is one of the fastest known enzymes with a turnover number of around $4 \times 10^7$ per second. Aqueous material above the filter carries the fluorescent material, or up converter (or we just observe the physical change in opacity).

In this embodiment the gelation is via ionic shift and is a precipitation that blocks the pores of the filter.

Conductivity or resistance could be measured in a final measuring step by putting an electric current across the liquid trapped above the filter In one embodiment, amylase can be used to produce the sugar portion of the same system from a starch-like substrate, and the overall reaction is the same. A transglutaminase enzyme of any type including TG1, TG2, TG3, TG5, FXIIIa or TGM; thrombin or any other serine protease capable of acting on fibrinogen or a suitable substrate can be used in combination with linker molecules that improve the degree of polymerisation. These molecules may include side groups or branching that can undergo cross-linking between the growing polymer chains on exposure to a reagent present in the final wash stage, such as derivatives of putrescine, cadaverine or acetal/carboxylic acid groups that will, in the presence of weak acid, expose hydroxyl groups and undergo esterification. Other methods are also possible, and will be apparent to those skilled in the art.

For transglutaminases, the substrates can include one or more of the following; Alpha-2 macroglobulin, AT1 receptor, collagen, coagulation factor V, fibrinogen alpha chain, fibronectin binding protein A, histidine-rich glycoprotein, laminin, myosin, semenogelin I, semenogelin II, thrombospondin, vinculin, Von Willebrand factor, vitronectin, actin, alpha-2 plasmin inhibitor, protein synthesis initiation factor 5a, fibrinogen, fibronectin, lipoprotein A, osteopontin, phospholipase A2, plasminogen, procarboxypeptidase B/U, uteroglobin, filaggrin, keratin filaments, loricrin, small proline rich proteins, desmoplakin, elafin, huntingtin, involucrin, galectin, glycogen, whey proteins, gelatin, bacteriorhodopsin, or any other species that can form a polymeric material on exposure to transglutaminases, as may become apparent to those skilled in the art. In some cases, such as whey proteins, a further wash with acid following the initial polymerisation stage to effectively crosslink and set the polymer may be required and is accounted for in this invention.

For thrombin or other serine proteases, a protein structure that cleaves to form an insoluble product, such as fibrinogen, is a suitable substrate.

For synthetic and protein-synthetic conjugate mixtures, the substrate can be any molecule that undergoes conversion by the catalytic species present in the probe to produce either a monomeric species that can undergo polymerisation, or one partner in a mixture of compounds that will undergo spontaneous and rapid formation of a highly cross-linked polymer network. For example, this method could include the use of starburst dendrimers with four pendant amine groups as one coupling partner, along with a protected bis-carbonyl substrate that undergoes cleavage to produce a bis-carbonyl linker capable of undergoing rapid amide formation with the dendrimer molecules. The resultant network would form a three-dimensional polymer network in the vicinity of the probes, and the concomitant trapping of optically-active particles would result. Other examples will be immediately apparent to those skilled in the art.

In a preferred embodiment, the conversion substrate is a pH sensitive protein (of biological origin) and more preferably a protein that precipitates in response to a pH change. Examples are globular proteins that are denatured by a pH change—such as albumen, bovine serum albumen, soy proteins, silkworm extract, casein or spidroins from spiders.

Alternative examples of fast turnover rate enzymes suitable for use in the invention are acetylcholine esterase (turnover between 500,000 and 12,333 molecules per second, depending on conditions). In this system, the enzyme can be linked to the probe and acetyl choline is added as a substrate. This produces acetic acid directly so there is no need for a secondary enzyme.

In another system carbonic anhydrase could be used, with a turnover number of 600,000. This enzyme converts carbon dioxide and water to carbonic acid. In this example the carbon dioxide substrate is provided by an excess of enzyme used to generate carbon dioxide such as, (but not limited to) phosphoenolpyruvate carboxytransphorphorylase in the presence of oxaloacetate and pyrophosphate in the medium. Examples 2 and 3 below refer to the use of carbonic anhydrase and acetylcholine esterase as the probe enzymes.

EXAMPLE 2 CARBONIC ANHYDRASE

The DNA and probe are attached to the membrane as in the catalase example, except that In this example carbonic anhydrase (bovine erythrocyte from Sigma-Aldrich) is attached to the probe instead of catalase. In this case there is no need for a secondary reaction to generate the acid, but there is a need to produce an excess of the substrate for the enzyme. Therefore, the final reaction is done by adding an excess of a carbon dioxide generating system, such as phosphoenolpyruvate carboxykinase (PEP carboxykinase), typically 0.01 ml/ml (SIGMA-Aldrich). The reaction is started by adding 10 mM oxaloacetate to the solution with some agitation to prevent premature precipitation of the casein with the pH change created by the oxaloacetate addition.

EXAMPLE 3 ACETYLCHOLINE ESTERASE

The DNA and probe are attached to the membrane as in the preferred catalase example, except that in this embodiment, acetylcholine esterase (ACHE) is attached to the probe (human recombinant from SIGMA Aldrich) in place the of catalase enzyme. The reaction is started by the addition of acetyl choline (10 mM). Since this enzyme produces acid directly there is no need for a secondary reaction.

The optically active particle should be a component that is insoluble in the buffer but sufficiently small to not block fluid flow across the slide surface. Sub-micrometre-sized phosphors can be used, and the surface of said phosphors can be altered to enhance cross linking with the substrate polymerisation, or to prevent any non-specific binding.

Alternatively, the particles can be colloidal silver or gold, and an optically-active dye species bound to the particles by surface interaction such as the strong interaction between sulfur groups and gold, or through electrostatic interaction.

In another variation of the invention, the optically-active species can be a dye or other molecule with a measurable optical response that is capable of or has been converted in such a way that it is incorporated into the three-dimensional polymer network as produced by the action of the probe. This can be either incorporation into the network (where the particle or molecule possesses two or more functional groups capable of undergoing spontaneous reaction) or reaction to a separate moiety on the growing or already-grown polymer network. This variation includes additional wash steps as required for activation for the grafting process, as should be evident to prevent premature grafting or inhibition of the polymerisation process.

Surface Assay

Following polymerisation and washing, the surface is assayed by exciting the optically active particles with light of a suitable wavelength from a source that may include broad-spectrum lamps with a suitable filter set-up, an LED array a laser or any other suitably energetic source. Light is focussed onto the surface and the emitted response from the optically-active particles is measured using a photomultiplier tube or a suitable spectrophotometer.

The measurement of a response above a certain threshold consistent with the signal required to distinguish the presence of the optically-active components above system noise within a preset time will return a positive result confirming the presence of particles, and hence by extension: polymer, catalyst, probe, and target sequence.

The apparatus is entirely controlled by a CPU; results are stored in said CPU, and presented to the user either through an LCD screen or using a series of coloured light emitting diodes.

A preferred embodiment of the invention will now be fully described with reference to the figures.

Figure 2:
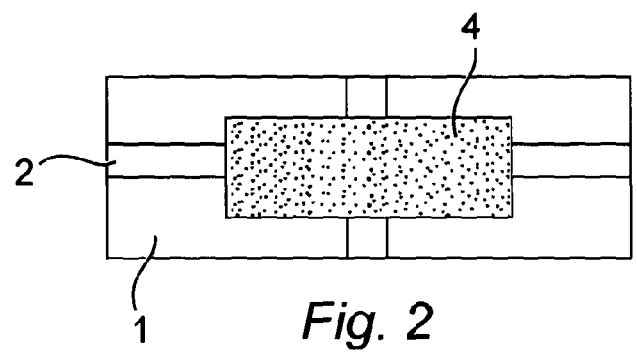
FIG. 2 shows a plan view of the disposable slide for oligonucleotide detection.

FIGS. 1 and 2 depict a device according to the present invention. The important structural elements are described as follows; a major supportive slide component formed from plastic or another suitable and relatively inert material, 1 (note that glass is not a suitable substitute in the preferred embodiment due to surface interactions with oligonucleotides), channels and a well 2 cut into the supportive slide 1 that allow ingress and egress of fluid, a clear cover slip 3 that covers the supportive slide 1, seals the top surface of all channels 2, and allows light in the visible and near-IR region pass through unobstructed, and a section of nitrocellulose 4 set into the bottom of the supportive slide 1, coincident with the well 2, that is supported by the surrounding materials but flow through and across it is not obstructed.

Figure 3:
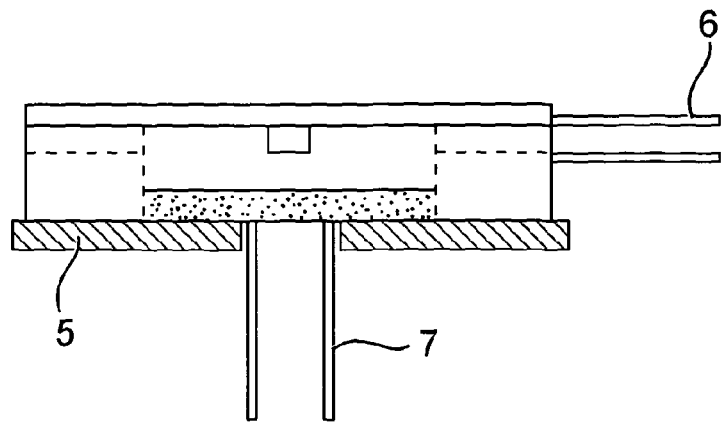
FIG. 3 shows a side view of disposable slide set up for application of oligonucleotide sample.

Turning to FIG. 3, the assay slide is arranged with apparatus for the application of a solution of oligonucleotide sample to the nitrocellulose membrane 4. The assay slide is held on a heating plate 5 and the sample solution is applied to the slide through one of the access ports via an injection head, 6. Negative pressure is applied to the rear side of the nitrocellulose slide using suction apparatus, 7, accessing the nitrocellulose slip 4 through a hole in the heating plate 5.

Figure 4:
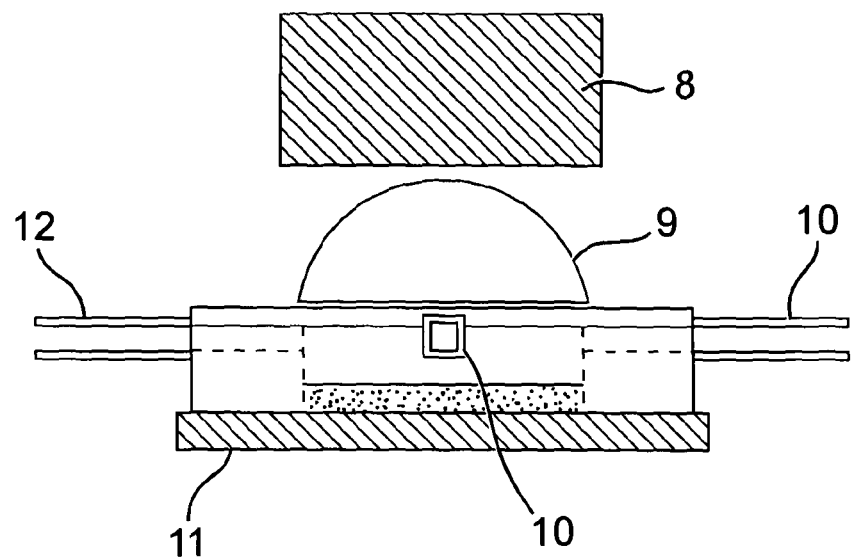
FIG. 4 shows a side view of disposable slide set up for assay and measurement.
Figure 5:
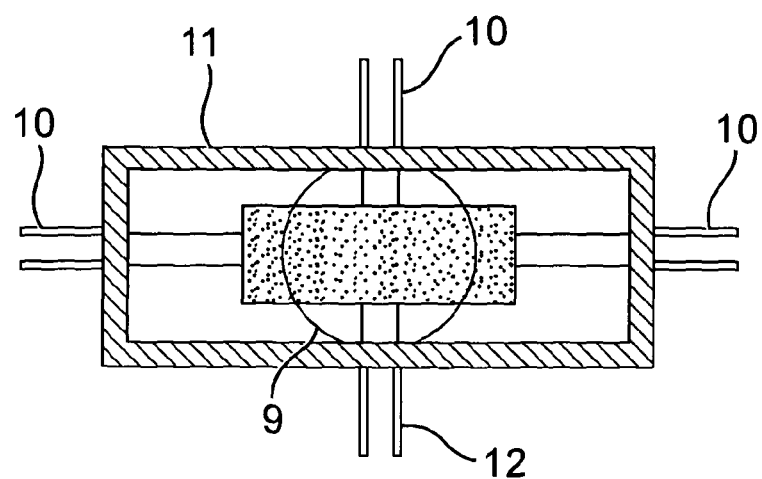
FIG. 5 shows a plan view of disposable slide set up for assay and measurement.

FIGS. 4 and 5 shows another view of the assay slide arranged with apparatus for the application of reagents, removal of waste reagents, and interrogation of the slide contents through the clear window or cover slip 3. Measurement of optical properties within the cell are taken using the joint application of a excitation/detection unit 8 which can be a combination of any light source capable of penetrating the cover slip 3 in the UV to near-IR range, and an optical spectrometer capable of measuring a range of wavelengths coincident with the emission wavelengths of the assay system. Suitable mirror and filter arrangements to prevent cross-talk between emission and excitation sources will be immediately apparent to those skilled in the art. In an alternative embodiment, the detector 8 may be a photomultiplier tube capable of measuring photonic emission in the visible spectrum. The preferred measurement is in the IR spectrum. A lens 9, which in this embodiment is a half-ball lens, is used to collect and focus the light emitted from the cell. In an alternative embodiment, the lens 9 may be a complete ball lens or another arrangement of optical filtering, focussing or manipulation apparatus as may be required to obtain optimum signal for the detector 8. Cell inputs, 10, are formed by close association of channels within the device and wells 2 in the slide, the alignment of which is controlled by precise control over the size of the device interior and the use of suitable spatial restriction to maintain a correct and suitable seal between the two.

A further development of this embodiment may include sealed fittings such that the two components interlock neatly although for the sake of clarity this is not illustrated in FIG. 4.

Control over the slide temperature is achieved by use of a heating plate, 12 which is in close contact with the rear of the slide throughout the experiment. Not only is heat applied via this method, but also support of the slide throughout measurement, preventing unwanted motion or misalignment of the slide during the assay. Waste fluids are permitted to egress the slide via a connection in the same manner that they are applied. Complete washing of the slide is carried out by use of an excess of fluid wash suitable to cause turbulent movement of fluid throughout the slide and thus retain simplicity in the design.

Figure 6:
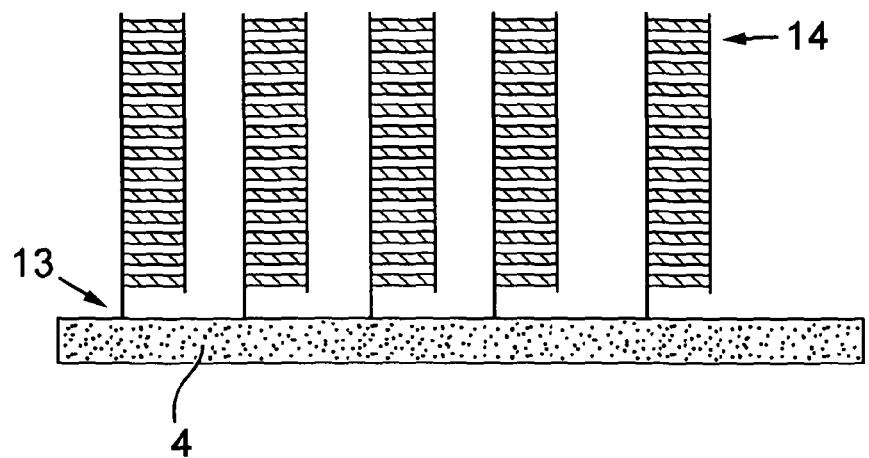
FIG. 6 shows an oligonucleotide sample bound to nitrocellulose surface prior to assay.

When a sample is provided to the device, the cells in the sample are lysed and the then exposed DNA is bound to the nitrocellulose 4. FIG. 6 shows an expanded view of a typical DNA sample, 14, bound to the nitrocellulose surface 4, following the application stage. Through heat treatment, the oligonucleotides have become physically bonded to the surface, 13. Extraneous proteins, salts, organics and other materials have been partially degraded by heat treatment and washed away. In an alternative embodiment, all protein materials can be separated by electrophoresis through a short path-length gel prior to sample application to the surface.

Figure 7:
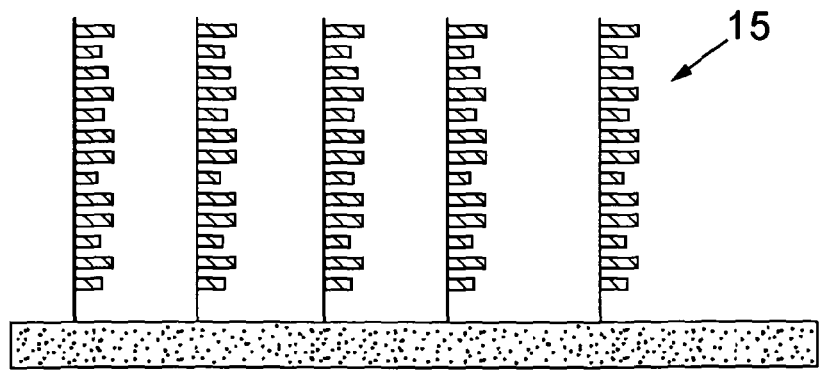
FIG. 7 shows an oligonucleotide sample bound to nitrocellulose surface following denaturation and wash steps.

When the DNA is bound to the nitrocellulose 4, the next step is to denature the DNA—this requires a temperature in the range 93-98 degrees centigrade depending on the nature of the oligonucleotide. FIG. 7 is an expanded view of the bound oligonucleotide sample following denaturation and washing. The double-stranded molecules have unwound and disassociated, 15.

Figure 8:
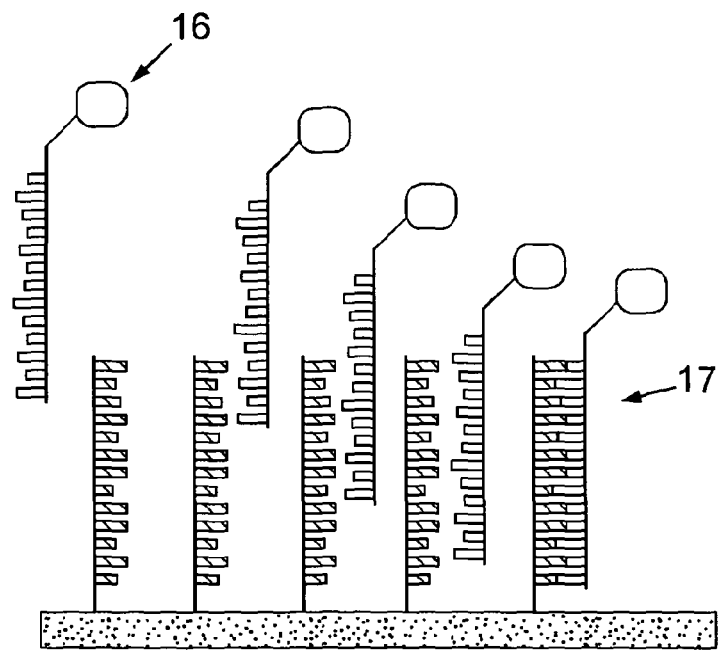
FIG. 8 shows a probe binding to oligonucleotide sample.

The next step is to add the probe such that it will hybridise to any complementary nucleic acid strands that are present. The temperature profile is lowered to a range falling between 50 and 65 degrees centigrade, again depending on the oligonucleotide and probes used. The surface is washed with a solution of the probe molecule 16 which binds spontaneously to the unwound oligonucleotide strands, 17. Note that only one probe is shown in the diagram for simplicity, but this technique could include several probes with unique sequences that correspond to different sections and both strands of the oligonucleotide. FIG. 8 shows an expanded view of the nitrocellulose-bound oligonucleotide sample during the probe association step.

Figure 9:
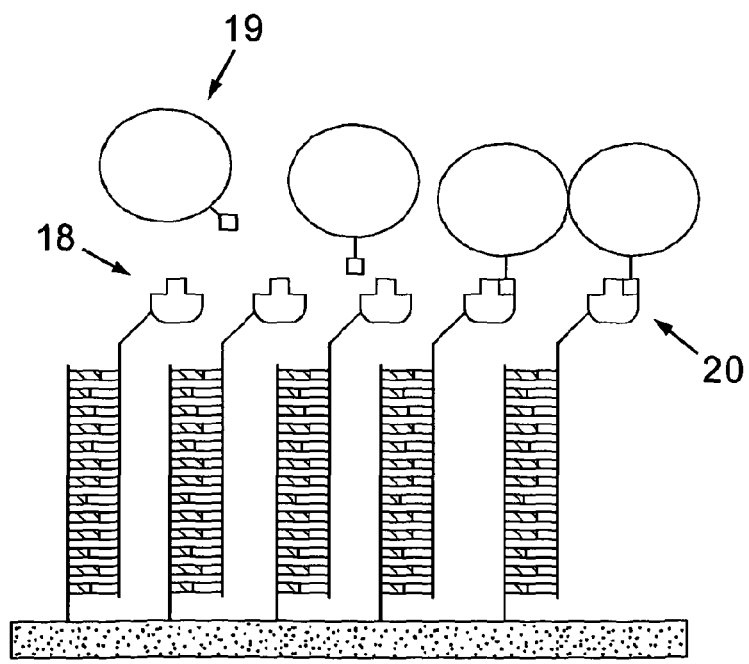
FIG. 9 Derivatisation of oligonucleotide-probe conjugate.

In certain embodiments of the invention, the probe does not comprise a catalytic element at this point, and it is necessary to incorporate it. FIG. 9 is an expanded view of a post-binding derivatisation reaction, where a catalytic group or enzyme, 19, linked to a binding agent is added to the slide and reacts spontaneously with the probe molecule (being capped with the second partner in the binding couple, 18) to create a conjugate of oligonucleotide, linker and catalytic or enzymatic group, 20, on the surface of the nitrocellulose 4. In an alternative embodiment, the probe is capped with the catalytic or enzymatic moiety prior to this stage, and the process of binding as described in FIG. 8 is sufficient to produce the desired result, as shown in FIG. 10.

Figure 10:
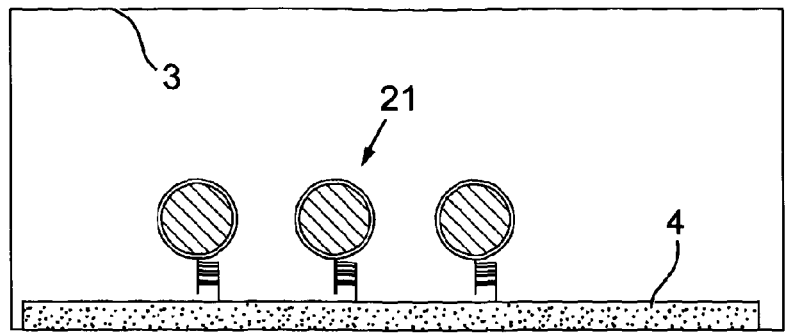
FIG. 10 shows a slide sample well following probe binding but prior to the polymerisation assay.

FIG. 10 is a view of the slide well 2 following the processes up to and including FIG. 9. The slide roof or cover slip, 3, being transparent to light, particularly light within the visible and near-IR regions of the electromagnetic spectrum, is shown above the nitrocellulose sample strip, 4, onto which is bound an array of sample oligonucleotide bound to a probe that terminates with a suitable enzymatic or catalytic group, 21.

Figure 11:
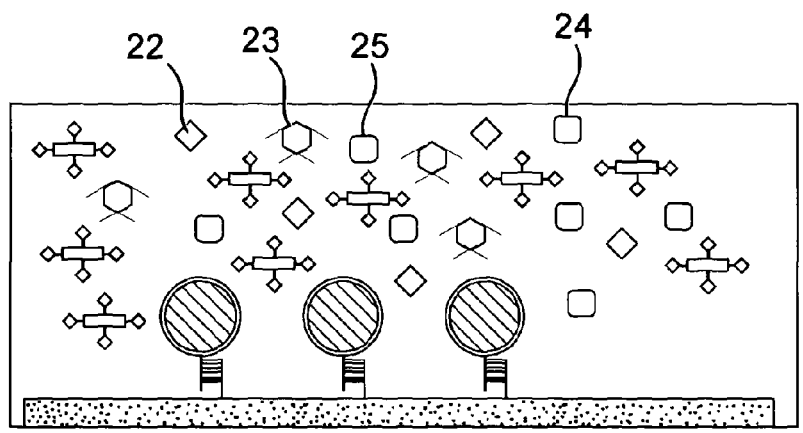
FIG. 11 Application of the polymerisation assay mixture, and reaction.

The next step is to add a polymerisation assay mixture which contains a substrate 22 for the catalytic or enzymatic moiety 19, a second catalyst species 23, a substrate for the second catalyst to act upon 24, and an optically active element 25. FIG. 11 is a side view of the slide well following addition of the polymerisation assay mixture. In this embodiment, the optically active element 25 is an insoluble particle capable of responding to interrogation via the optical apparatus described in FIG. 4. In an alternative embodiment, this particle can be derivatised with specific molecular groups such that the particles have a strong association with the final polymer product, or are physically bound via covalent bonding to become part of the polymer network itself. In yet another variation of this embodiment, an optically active molecule that can participate in the polymerisation and is soluble in the carrier solvent is used. The substrate 22 is a monomer or a mixture of monomers that are soluble in the carrier solvent and will undergo a polymerisation process only in the presence of the enzyme or catalyst bound into the surface array, 21. An example of this embodiment is the use of fibrinogen; this is a water soluble protein that, in the presence of thrombin, undergoes a reaction to form insoluble strands of fibrin in a process called the coagulation cascade.

Figure 12:
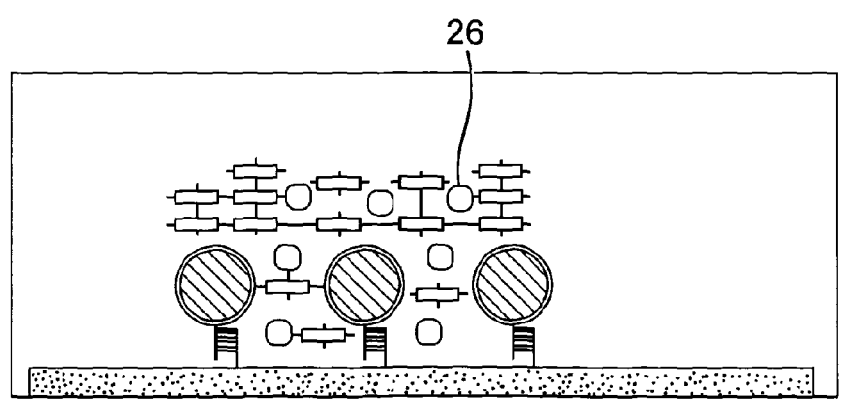
FIG. 12 Slide sample well, post polymerisation reaction and wash steps.

FIG. 12 shows a slide view of the slide well following completion of the polymerisation process and subsequent wash steps to remove the unused monomer and unbound optically-active particles. In a negative test scenario, where no enzyme was present, this washing stage would remove all of the monomer unreacted, and all of the optical material. However, in the presence of the relevant catalyst or enzyme 21, a polymer network has formed and optically active particles have become trapped, bound or bonded to the polymer network, 26, depending on their specific properties.

Figure 13:
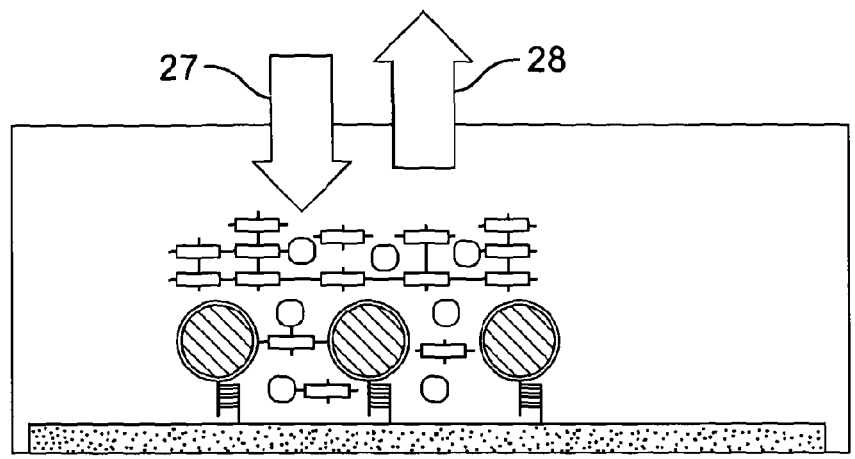
FIG. 13 Interrogation of the sample well using optical apparatus.

FIG. 13 is the final stage of the assay. The optical apparatus as described in FIG. 4 is used to interrogate the sample using an excitation wavelength, 27, and measuring the emission wavelength, 28.

In an alternative embodiment of the invention, the assay and measurement stage are combined at the point of FIG. 11—in this embodiment the addition of a reactive mixture that can undergo degradation in the presence of the enzyme and hence follow a reactive path that produces a photonic response, such as chemiluminescence is followed. In this alternative embodiment, no excitation is required, and the detection instrument is a photomultiplier tube reading a cumulative total of photons released, 28. Alternatively a photodiode could be used.

It can be seen that the present invention has a number of benefits over the prior art and has a wide range of potential uses.

Another method of determining presence of a specific moiety includes an immobilised sample in multi-well sample plates. This would use the principles of the testing method in a well-format and replace the mechanical processing of the steps with manual operation. This enables many more samples to be processed at one time utilising a reasonably skilled laboratory technician manipulating the many wells simultaneously. The detection mechanism of this testing method could be linked to an agent able to specifically bind to another component of the sample to be tested.

The invention claimed is:

1. A method of testing for the presence of a target nucleic acid sequence, target protein or target antigen comprising the steps of:
    exposing nucleic acid sequences, proteins or antigens from a sample to a probe under hybridisation conditions;
    the probe comprising a first catalytic element or precursor thereof and a binding element capable of binding at least partially to the target nucleic acid sequence, target protein or target antigen;
    exposing the nucleic acid sequences, proteins or antigens to:
    identifiable marker elements;
    at least a first substrate, said substrate being capable of reaction with the first catalytic element;
    and a conversion substrate;
    under conditions which result in a physical change of the conversion substrate and the physical change causes the identifiable marker elements to be entrapped or otherwise retained against removal by washing, substantially in the vicinity of the probe; and,
    wherein the first catalytic element is a catalytic element that is capable of a turnover rate of greater than 3000 molecules per second.

2. A method according to claim 1, wherein the conditions comprise the step of exposing the nucleic acid sequences to a second substrate and a second catalytic element.

3. A method according to claim 2, wherein the product of the reaction of the first substrate and first catalytic element comprises a catalyst or substrate for the reaction of the second substrate and second catalytic element.

4. A method according to claim 1, wherein the nucleic acid sequences are exposed to a conversion substrate.

5. A method according to claim 4, wherein a physical change of the conversion substrate is effected by the product of the reaction of the first substrate and first catalytic element and/or the product of the reaction of the second substrate and second catalytic element.

6. A method according to claim 1, wherein the physical change comprises a pH change, degeneration, gelation, coagulation, precipitation, change in optical density, change in colour, change in fluorescence, polymerization and/or cross-linking.

7. A method according to claim 6, wherein the physical change comprises formation of a three dimensional polymer network.

8. A method according to claim 1, comprising the preliminary steps of:
    rendering the nucleic acid sequences available, and immobilising the nucleic acid sequences.

9. A method according to claim 1, further comprising at least one washing step.

10. A method according to claim 1, comprising a final washing step wherein the wash comprises a reagent that promotes cross-linking of polymer chains.

11. A method according to claim 1, wherein the identifiable elements are identifiable by photonic, optical or electrical measurement.

12. A method according to claim 11, comprising the step of detecting a photonic response using a photomultiplier tube or photodiode.

13. A method according to claim 1, wherein the identifiable elements comprise optically active particles.

14. A method according to claim 13, wherein the optically active particles are sufficiently small to not block fluid flow across a slide surface.

15. A method according to claim 13, wherein the optically active particles comprise substantially sub-micrometer sized phosphors.

16. A method according to claim 13, comprising the step of testing for the presence of identifiable components by exciting the optically active particles with light and measuring the response.

17. A method according to claim 16, further comprising the step of comparing the response to a predetermined threshold value.

18. A method according to claim 1, wherein the binding element is an oligonucleotide sequence complementary to the target nucleic acid sequence.

19. A method according to claim 1, wherein the method detects the presence or absence of a micro-organism of interest in the sample.

20. A method according to claim 19, wherein the micro-organism is MRSA.

21. A method according to claim 1, wherein the catalytic element comprises at least one catalytic precursor and the method comprises the step of exposing the nucleic acid sequences or proteins or antigens to an activating element that adds a catalyst to the at least one catalytic precursor binding site or reacts with the at least one catalytic precursor to form a catalyst.

22. A method according to claim 1, wherein the first catalytic element comprises catalase and the first substrate comprises a peroxide.

* * * * *